US007959739B2

(12) United States Patent
Beck

(10) Patent No.: US 7,959,739 B2
(45) Date of Patent: Jun. 14, 2011

(54) PARTICLE REMOVAL CLEANING METHOD AND COMPOSITION

(75) Inventor: Mark Jonathan Beck, Los Gatos, CA (US)

(73) Assignee: Fontana Technology, Campbell, CA (US)

( * ) Notice: Subject to any disclaimer, the term of this patent is extended or adjusted under 35 U.S.C. 154(b) by 0 days.

(21) Appl. No.: 12/330,478

(22) Filed: Dec. 8, 2008

(65) Prior Publication Data

US 2009/0149364 A1 Jun. 11, 2009

Related U.S. Application Data

(60) Provisional application No. 61/012,125, filed on Dec. 7, 2007.

(51) Int. Cl.
*B08B 3/04* (2006.01)
*C11D 3/37* (2006.01)

(52) U.S. Cl. .......... 134/2; 134/38; 134/39; 134/41; 134/42; 510/165; 510/166; 510/167; 510/168; 510/170; 510/175; 510/423; 510/434; 510/476; 510/499; 510/504

(58) Field of Classification Search .......... 510/165, 510/166, 167, 168, 170, 175, 423, 434, 476, 510/499, 504; 134/2, 38, 39, 41, 42
See application file for complete search history.

(56) References Cited

U.S. PATENT DOCUMENTS

| | | | |
|---|---|---|---|
| 2002/0072482 A1* | 6/2002 | Sachdev et al. | 510/175 |
| 2002/0189635 A1* | 12/2002 | Bodet et al. | 134/1 |
| 2003/0144163 A1* | 7/2003 | Morinaga et al. | 510/175 |
| 2009/0056744 A1* | 3/2009 | Carswell | 134/1.3 |

* cited by examiner

*Primary Examiner* — Brian P Mruk
(74) *Attorney, Agent, or Firm* — Donald J. Pagel

(57) ABSTRACT

A cleaning solution and method for removing submicron particles from the surface and/or the bevel of an electronic substrate such as a hard disk media substrate, or an imprint mold used in the manufacturing of the hard disk media or a read/write head assembly part. The cleaning solution comprises a polycarboxylate polymer or an ethoxylated polyamine. The method comprises the step of contacting a surface of the substrate with a cleaning solution comprised of a polycarboxylate polymer or an ethoxylated polyamine. Additional optional steps in the method include applying acoustic energy to the cleaning solution and/or rinsing the surface with a rinsing solution with or without the application of acoustic energy to the rinsing solution.

8 Claims, 4 Drawing Sheets

PARTICLE REMOVAL CLEANING METHOD AND COMPOSITION

This application claims the benefit of U.S. provisional application 61/012,125, filed Dec. 7, 2007, which is incorporated herein by reference.

BACKGROUND OF THE INVENTION

As presently practiced, particle removal is usually achieved by a combination of mechanical and chemical mechanisms. In hard disk manufacturing special dedicated tools are used to scrub or remove particles, often called scrubbers. In many such scrubbers a mechanical particle removal method is used simply with room temperature or sometimes heated DI (deionized) water. Chemicals can be added to enhance the removal efficiency. Cleaning tools differ from scrubbers in that mechanical removal techniques are combined with chemicals instead of simple DI water to remove particles both with a mechanical method and a chemical method combined. Additionally in a cleaning tool, other functions can also be performed in addition to particle removal. For example, the removal of metallic impurities, organic impurities and even wet etching of layers and wet stripping of photoresist can be performed in a cleaning tool in addition to the particle removal function that is the object of this invention.

In a scrubber or cleaning tool for hard disk manufacturing usually a combination of ultrasonics, megasonics and brushes is used to clean the hard disk media, imprint molds and read/write head assembly part. A variety of chemicals is added for removal of particles from hard disk media.

Before the invention of megasonics, ultrasonics was used. Ultrasonics has frequencies in the range of 20 kHz to about 120 kHz.

In the hard disk industry a variety of frequencies are used ranging all the way from 40 kHz up to 1 MHz. Quite often in the hard disk industry a frequency of about 400 kHz is being used.

It is now widely accepted that, in case when there is no mechanical particle method added to the chemistry, and therefore, when particle removal is achieved by chemical contacting only, then the contacting chemistry simply removes particles due to underetching of the particle. The underetching theory goes as follows: a controlled amount of the surface layer is uniformly removed or etched all over the surface of the substrate to be cleaned, usually a hard disk substrate or an imprint mold or a head assembly part. When etching this surface layer, the material underneath the particle is also etched away and this etching releases the particle from the surface. Then, the particle is washed away.

Since the current state of the art for removing particles by chemical means only, relies on undercut etching, and since etching increases with temperature, everyone so far has found that particle removal efficiency increases with temperature.

Megasonics on the other hand relies on cavitation to remove particles and cavitation is not very much temperature dependent. However, since cavitation is very dependent on the dissolved gases, it has been found that megasonics vibration doesn't remove many particles when there are no gases present.

Currently, a cleaning paradox has emerged. Megasonics vibration works well for removing particles and with a very wide temperature range, but the cavitation which the megasonics produces, and which is used to remove particles, also damages the fine patterns and advanced hard disks are starting to use such finely patterned surfaces. Also the imprint molds used for manufacturing hard disks have very fragile patterns. Indeed, the patterns on the hard disks and imprint molds in advanced technologies of hard disk manufacturing are becoming so small that they are very fragile and are very prone to mechanical damage. Now with pattern sizes sometimes as small as 22 nm in 1 dimension, any megasonics power or rather any cavitation will destroy such patterns. Megasonics damage starts to be a problem when the pattern sizes become smaller than 0.3 µm.

Therefore, a new method for removing small particles from the surface of the disks and imprint molds without damaging the fragile structures is necessary. The underetching mechanism, which does not damage the fragile structures, however can also not be used anymore, since the structures are so small, that underetching would remove valuable material from the surface. This is the current cleaning paradox that we are faced with.

Hence the paradox: mechanical particle removal cannot be used anymore for small particle removal, since it also damages the fine patterns, and conventional chemical particle removal by underetching cannot be used anymore, because of loss of surface material which is now a substantial part of the surface.

Even in those cases where the substrate is completely flat and where damage is not a paramount concern, it has been found that for very small particles, the mechanical methods are not effective anymore. Mechanical methods to remove particles, such as, but not limited to, brush scrubbing, spray aerosol bombardment, and ultrasonic and megasonic vibration, are very effective for the large particles, but loose efficiency for the very small particles. Hence, there is a need for an improved chemical method to remove these very small particles even on substrates without patterns. This is the case for current generation hard disks. This is also the case for the read/write head assemblies.

As a summary, there is a great need in the hard disk industry for a solution and a method and an apparatus that can remove small particles from the front side or back side of hard disks and imprint molds without damaging the fine patterns and without substantial underetching of the surface material. There is a general need for an improved chemical method to remove small particles even on substrates without pattern such as conventional hard disks and on read/write head assemblies.

More generally, none of the presently known methods can efficiently remove very small particles, since most of the mechanical techniques loose efficiency for small particles and most of the currently known chemical methods are not very effective for very small particles. The prior art does not provide for an improved chemical method to remove very small particles more efficiently.

BRIEF SUMMARY OF THE INVENTION

Briefly, the present invention is a method and cleaning solution for cleaning a hard disk media (hard disk), or an imprint mold used in the manufacturing of a hard disk or a read/write head assembly part. The method comprises the steps of contacting a surface of the part with a cleaning solution comprised of a polycarboxylate polymer or an ethoxylated polyamine; and then removing the cleaning solution from the surface. Additional optional steps in the method include applying acoustic energy to the cleaning solution and following the cleaning by rinsing the surface with a rinsing solution with or without the application of acoustic energy to the rinsing solution.

The cleaning solution of this invention is used for removing submicron particles from the surface and/or the bevel of an electronic substrate such as a hard disk media substrate or an imprint mold used in the manufacturing of such hard disks, or a read/write head assembly part. The cleaning solution comprises a polycarboxylate polymer or an ethoxylated polyamine. The polycarboxylate polymer of the present invention comprises homopolymers or copolymers of acrylic acid, methacrylic acid, maleic acid, fumaric acid, itaconic acid, and the like. Alternatively an ethoxylated polyamine is used in the solution to remove particles from the surfaces and or bevel of an electronic substrate such as a hard disk or an imprint mold used in the manufacturing of such hard disks or a read/write head assembly part.

The solution which either contains a concentrated polycarboxylate polymer or a concentrated ethoxylated polyamine or both and may also additionally contain a base or an acid, can be delivered in concentrated form and then diluted at point of use and then dispensed or contacted on the surface or the bevel of an electronic substrate such as a hard disk or imprint mold used in the manufacturing of such hard disk or a read/write head assembly part. The dispensing and/or cleaning and/or rinsing optionally can be carried out at subambient temperatures. A base such as ammonium hydroxide, tetramethylammonium hydroxide, choline can be added and in addition or alternatively, an amine such as monoethanolamine and a biocide can be added. Alternatively or in addition, a surfactant and/or a sequestering agent can be added.

After dilution or even undiluted, any of the solutions of the invention can be used in a method to clean the surface of an electronic substrate such as a hard disk or an imprint mold used in the manufacturing of such hard disks.

The solution can also be used to clean the bevel of the electronic substrate such as a hard disk. The bevel can be cleaned with e.g. a brush or a megasonic nozzle together with the solution of this invention.

After cleaning the surface or the bevel with any of the solutions of this invention, the solution needs to be rinsed from the hard disk and/or bevel surface. The rinsing step can also be assisted with a spray or brush or with megasonics, without causing damaging cavitation if fragile structures are present on the surface. The damaging cavitation can be avoided by either not using dissolved gas or by using high frequency megasonics.

BRIEF DESCRIPTION OF THE SEVERAL VIEWS OF THE DRAWING

The invention is best understood from the following detailed description when read in connection with the accompanying drawings. It is emphasized that, according to common practice, the various features of the drawing are not to scale. On the contrary, the dimensions of the various features are arbitrarily expanded or reduced for clarity. Included are the following figures.

DETAILED DESCRIPTION OF THE INVENTION

Figure 1:
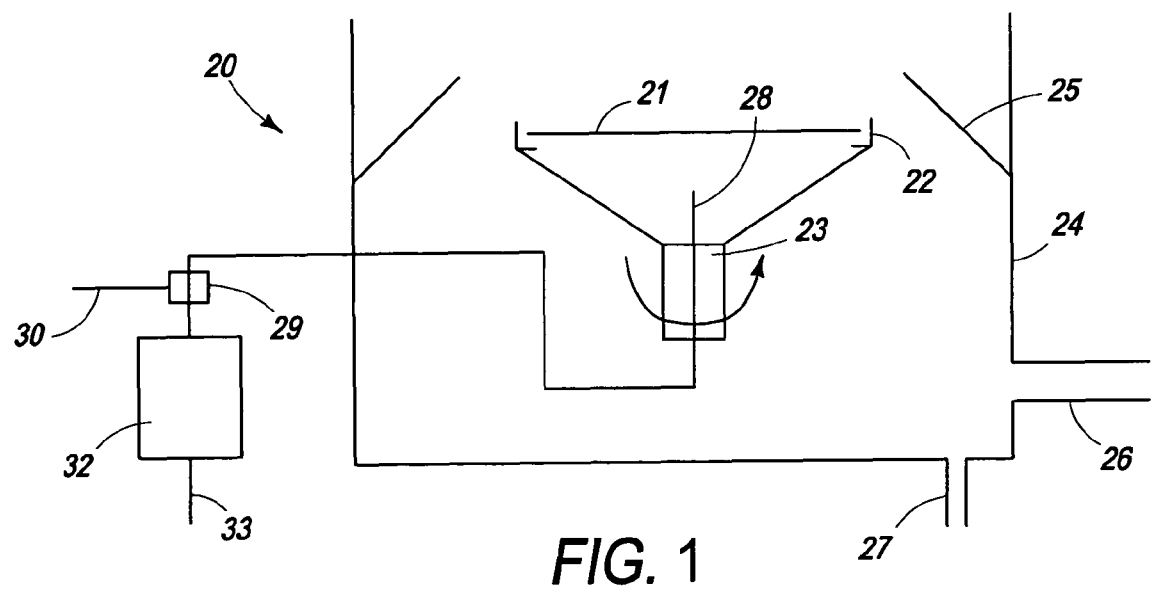
FIG. 1 is a schematic diagram of a single imprint mold spin-spray system according to the present invention for removing small particles from the front side of the imprint mold.
Figure 2:
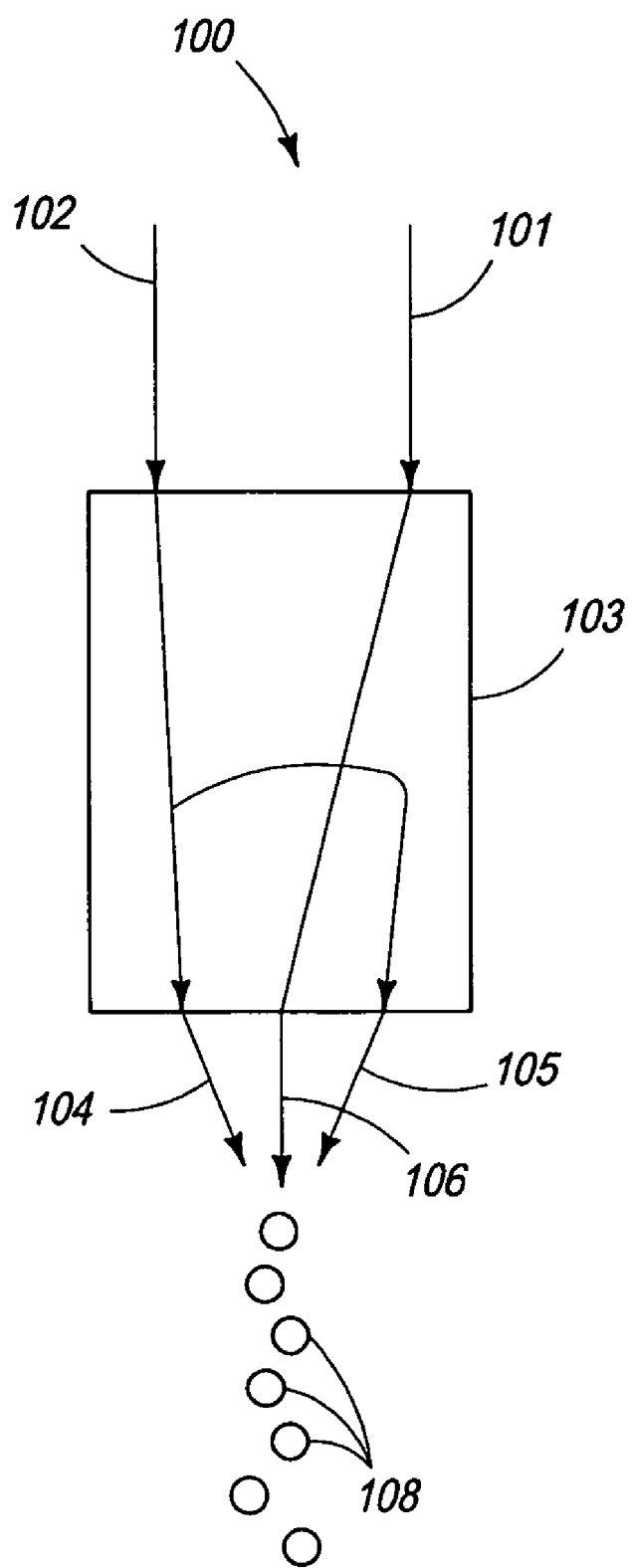
FIG. 2 is a schematic representation of a nozzle where the solution of polycarboxylate polymer or ethoxylated polyamine is accelerated by an $N_2$ or CDA gas flow outside the nozzle body.
Figure 3:
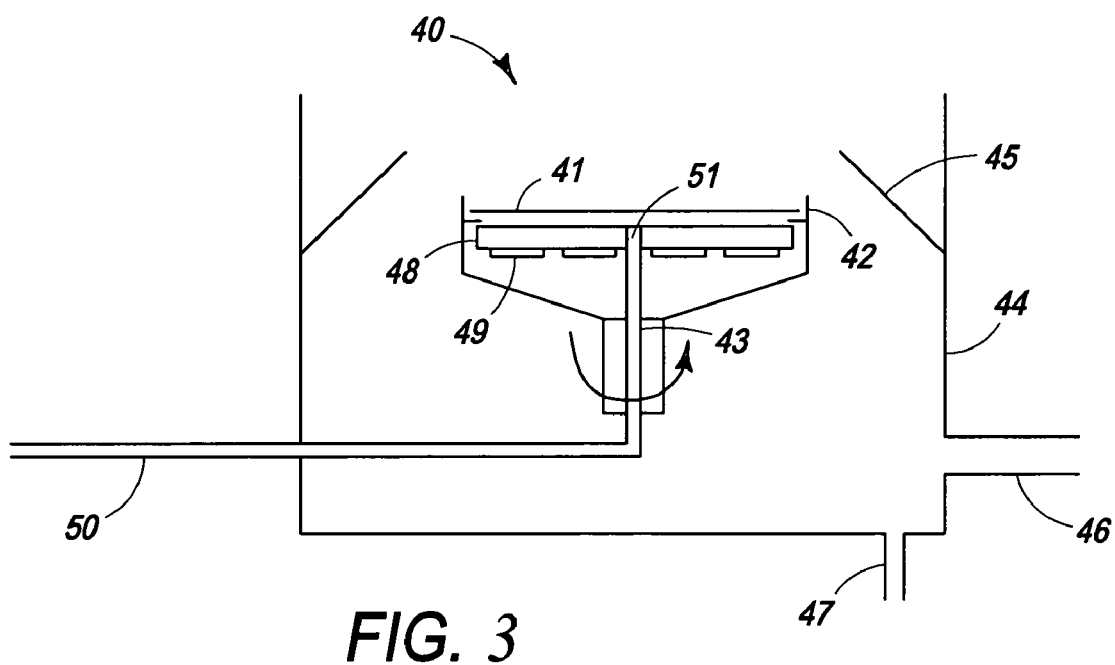
FIG. 3 is a schematic diagram of a single imprint mold spin-spray system according to the present invention for removing small and large particles from the front side of the imprint mold.
Figure 4:
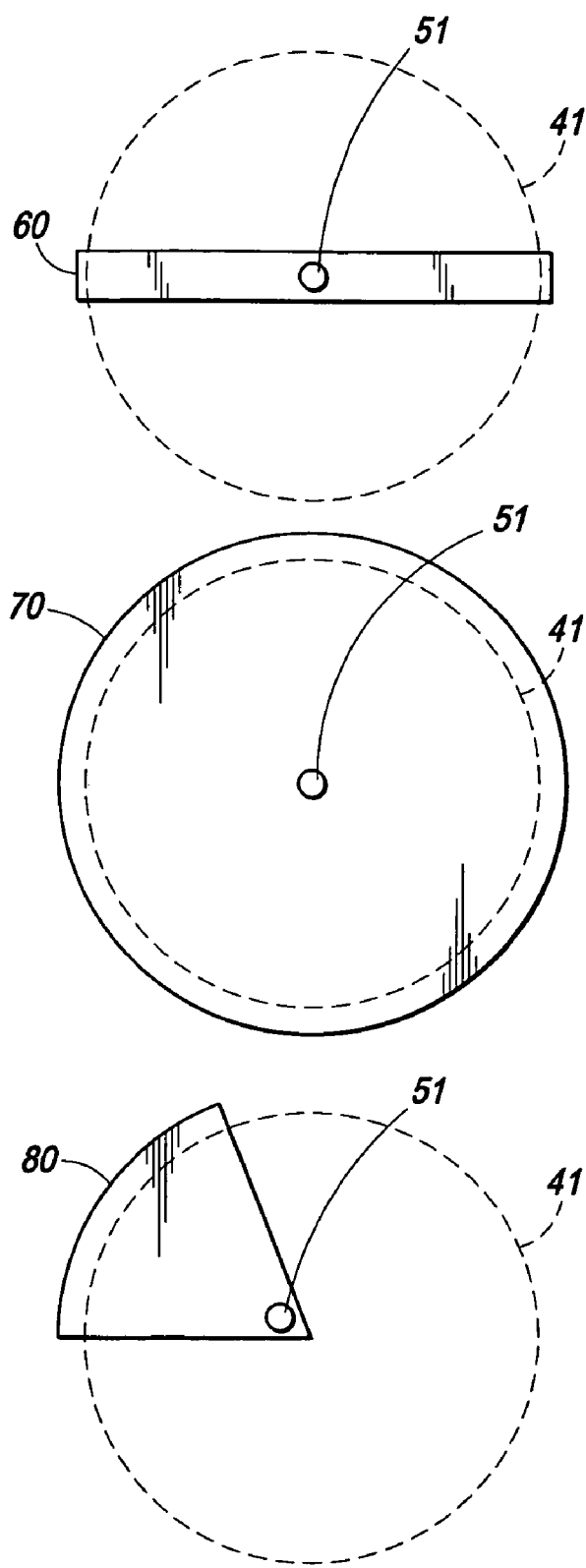
FIG. 4 is a schematic top view of various transducers that can be used in the preferred embodiment shown in FIG. 3, positioned below the imprint mold.

A cleaning solution used in the present invention comprises a polycarboxylate polymer solution. In one embodiment, the polycarboxylate polymers may comprise homopolymers or copolymers of acrylic acid, methacrylic acid, maleic acid, fumaric acid, itaconic acid and the like. When the term homopolymer is used, it is intended that it includes by definition, polymers that may contain quantities of about 20 mole percent or less, of one or more comonomers. In other words, a polymer containing up to 20 more percent of comonomers will still be considered a homopolymer. The cleaning solution may also comprise a blend of the above polycarboxylate polymers.

Particularly suitable polycarboxylate polymers are prepared from monomers having the general formula (Formula 1):

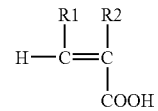

Where R1 and R2 is either a hydrogen atom (H) or methyl radical ($CH_3$, also represented by Me).

A polycarboxylate polymer (homopolymer) formed from monomers of this type can be schematically represented by the following formula (Formula 2):

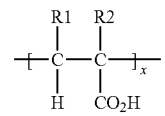

Where R1 may be H or COOH (carboxyl); and R2 may be H, Me or $CH_2COOH$.

In specific embodiments, the monomer may be acrylic acid (R1 and R2 are H) or methacrylic acid (R1=H and R2=Me). In other embodiments, the monomers may be maleic acid R1=COOH and R2=H, with the carboxylic acid groups in the cis configuration); fumaric acid (R1=COOH and R2=H, with the carboxylic acid groups in the trans configuration); and itaconic acid (R1=H and R2=$CH_2COOH$). Polycarboxylate polymers (copolymers) comprising combinations of these monomer units may also be used (e.g. Formula 5, below).

Other suitable polymers are a maleic/olefin copolymer. This embodiment of the polycarboxylate polymer comprises a copolymer derived from maleic anhydride and a lower olefin. Preferably the maleic anhydride monomer has the following formula (Formula 3):

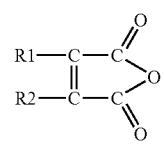

where R1 and R2 are independently H, an alkyl or a phenyl group. Most preferably R1 and R2 are H. The lower olefin component is e.g. ethylene, propylene, isopropylene, butylene or isobutylene and most preferably ethylene. This maleic/olefin copolymer can be added to a suitable acrylic acid or methacrylic acid homopolymer or copolymer. The maleic/olefin copolymer has the formula (Formula 4):

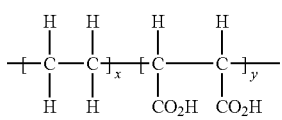

Other suitable polycarboxylate polymers are polymaleic acids, i.e., homopolymers of maleic acid. Still other suitable polycarboxylate polymers are acrylic acid/maleic acid copolymers which can be represented schematically by the following formula (Formula 5):

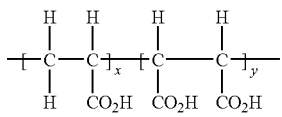

Formula 5 is a copolymer of polyacrylates and polymaleates. In the schematic representation above, the first group is an acrylate group and the second group is a maleate group.

An acrylic homopolymer can be schematically represented by the following structure (Formula 6):

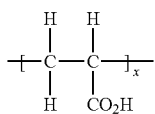

The average molecular weight of the polycarboxylate polymers given by Formulas 1-6 can vary between 300 and 1000000 Dalton. Preferably the average molecular weight is between 500 and 200000, even more preferably between 1000 and 80000 and most preferably between 2000 and 10000.

A particularly good copolymer for use in the present invention is a 50/50 acrylic/maleic copolymer (Formula 5) with an average molecular weight of about 3000 Dalton.

Such an acrylic acid/maleic acid copolymer, or an acrylic homopolymer, or a polycarboxylate polymer in general is typically synthesized by a raw material supplier and is typically made available in either the acid form or in a neutral form where the acid carboxylic groups are neutralized by a cation, most often Na$^+$ (sodium). It can also be in the ester form. When sodium is of no concern, as e.g. in certain cleaning operations for hard disks or in any general situation where sodium is of no concern, any supplied form will be appropriate. In cases where sodium is a concern, such for other specific cleaning operations in hard disks, then the acid form is preferable to use as the starting raw material for the cleaning solution blend. In the above schematic representations of the polymers, typically the acid form is shown. For the Na$^+$ neutralized form, the $CO_2H$ group in the formula above should be replaced by a $CO_2Na$ group.

For the cleaning solution of this invention, water soluble salts of carboxylic polymers as described above are especially preferred. The water soluble salt can be preferably an alkali metal, ammonium or substituted (quaternary) ammonium salt. The carboxylic polymers are converted to the desired salt by reaction of the acid form with the appropriate base. A typical alkali free soluble salt can be made by reaction of the polymer in the acid form with e.g. ammonium hydroxide, tetramethylammonium hydroxide or choline. For cleaning hard disk media alkali metals generally can be used. The alkali metals can be preferably sodium or potassium, with potassium being mostly preferred from a solubility and performance point of view. If cost is the main concern, then the sodium salt is preferred.

Typically the polycarboxylate polymer of this invention is added to a base in concentrated form at the chemical solution blending plant. Quite often the base will be NH$_4$OH, but it can also be TMAH (Tetra Methyl Ammonium Hydroxide) or choline or any other base that is suitable for the cleaning operation. Alternatively the base will be KOH or NH$_4$OH, but any other base can be used as well. This concentrated solution is then typically shipped to the manufacturing plant where the cleaning operation will be performed. At this manufacturing plant, the concentrated solution will be diluted with H$_2$O and or other chemicals to make up the cleaning solution. However, the polycarboxylate polymer can also be shipped in the acid form and then the base gets added at the fab, where the cleaning operation is performed.

Alternatively to the polycarboxylate polymers, an ethoxylated polyamine can be used in a cleaning solution to remove particles.

Schematically, an ethoxylated polyamine for use according to this invention has the following general formula (Formula 7):

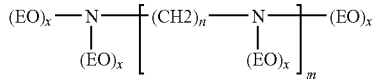

where EO is the oxyethylene moiety (—CH$_2$CH$_2$O—). The preferred ranges are as follows: the value of x ranges from 1 to 100, the value of n ranges from 1 to 30 and the value of m ranges from 1 to 30. The last EO is typically terminated with H (not shown in the schematical formula). A particular useful ethoxylated polyamine is the ethoxylated pentamine where x=15, n=2 and m=4. Schematically, the structure of the ethoxylated pentamine, which is very useful for the current invention, is as follows (Formula 8):

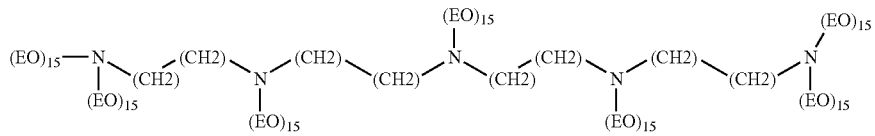

Another useful compound for use in the current invention is the ethoxylated, quaternized diamine with the following structure (Formula 9):

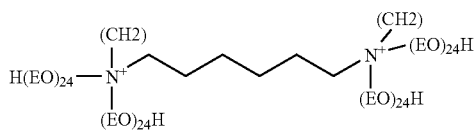

The ethoxylated polyamine of this invention will typically be added in concentrated form to make up a chemical solution in the blending plant. Typically the ethoxylated polyamine will be blended into either a neutral solution or an acidic solution.

Both the polycarboxylate polymer solution and the ethoxylated polyamine can be supplied as a concentrated solution without base. However, when using the polycarboxylate polymer solution for cleaning hard disks or imprint molds or read/write head assembly parts, the final blended cleaning solution is typically used at alkaline pH values, preferably in excess of pH 8. Potassium or ammonium hydroxide, or other bases, are typically added to increase the pH of the solution. This can be done at the chemical manufacturing or blending plant, but it can also be done at point of use. The ethoxylated Polyamine on the other hand can be used over a wide pH range and is not limited to alkaline pH cleaning when using this for cleaning hard disks or imprint molds or read/write head assembly parts. Finally, Surfactants and chelating agents can also be added.

After dilution of the source solution in the fab for cleaning use, the final concentration of the polycarboxylate polymer in the cleaning solution for cleaning the substrates and parts is preferably between 0.001%-6% by weight. More preferably the concentration of the polycarboxylate polymer in the cleaning solution is between 0.01% and 2% and most preferably the polycarboxylate polymer in the cleaning solution is between 0.1% and 1%. A particular good and effective concentration is about 0.6% for fast cleaning, but the cleaning effect of the polycarboxylate polymer on hard disks and imprint molds and read/write head assembly parts can even be observed down to 0.001%. There is a trade-off between concentration and cleaning time. At lower concentration the cleaning effect of the polycarboxylate polymer can be observed at longer cleaning times, whereas at higher concentration, even for short contacting times, the cleaning effect is already clearly seen.

When using the ethoxylated polyamine for cleaning hard disk media, and imprint molds and read/write head assembly parts, the concentration ranges for the ethoxylated polyamine are preferably at concentrations between 0.001% and 5% and more preferably between 0.01% and 2% ad most preferably between 0.1% and 1%.

Typically, the polycarboxylate polymer or the ethoxylated polyamine can be supplied to the fab in a concentrated solution, which can then be diluted with DI water and with other chemicals at point-of-use or centrally in the fab to yield the final cleaning concentration. The polycarboxylate polymer in a concentrated source solution can be supplied close to its solubility limit in such a source solution in order to reduce transportation expenses, but substantially lower concentrations can be used as well e.g. to suppress raw material costs and hence to reduce the final sales price of the blended chemical. Other reasons to supply a lower concentration is e.g. if the fab is using equipment that is set up for diluting the source concentration in a pre-fixed dilution ratio. E.g. typical dilution ratios used in fabs are 5 times such as used e.g. in a 5:1 bath. In that case, the polycarboxylate polymer concentration, when supplied together with e.g. the $NH_4OH$ in 1 solution, will need to be substantially lower in the source solution in order to give the right concentration after diluting according to such a pre-fixed ratio. Alternatively, the fab may not be set up to handle any dilution and will require the cleaning solution supplied at the use concentration. The solubility of the polycarboxylate polymer depends on its molecular weight. For this invention, polycarboxylate polymers with a molecular weight between 300 and 1 000 000 Daltons can be used. Higher molecular weight polycarboxylate polymers will be less soluble than lower molecular weight polycarboxylate polymers. Average molecular weight numbers (3000-70 000 Daltons) will typically have a solubility of about 40-60%-w in water. Therefore generally the solution can be supplied to the fab in concentrations ranging anywhere from 0.001% to 60%. However, higher concentrations are more economical with respect to transport and can be diluted at higher ratios in the fab.

Ethoxylated polyamines are substantially less soluble. The ethoxylated pentamine e.g. has a solubility of about 5%-w in water.

Typically, the source solution supplied by the chemical blending operation will be used in the fab for cleaning either straight (i.e. undiluted), or diluted, but diluted with water and/or other chemicals is preferable for economic reasons. It is clear that transporting a concentrated solution and diluting it at point-of-use with local DI water is more economical than diluting at the chemical blending company and then transporting the diluted solution over long distances.

When diluting the source solution, dilution ratios will be preferably between 5 and 10 000 times with DI water to make up the substrate cleaning solution, more preferably 5 to 1000 times, and most preferably 5 to 100 times. Besides dilution with water, other chemicals can be added as well.

When ammonium hydroxide is added to the concentrated source solution to make a source solution containing polycarboxylate polymer and ammonium hydroxide, it can be added in a concentration range of 1%-28%-w (weight of $NH_3$) to make a source solution consisting of ammonium hydroxide and polycarboxylate polymer. But any other suitable base can be used instead of ammonium hydroxide for making up the source solution. In various hard disk manufacturing operations specifically, KOH can be used as the base for cleaning solutions instead of ammonium hydroxide.

The source solution may also contain from 0.01% to 40% of an organic amine. Suitable organic amine compounds may be selected from alkanolamines (e.g. primary alkanolamines:

monoethanolamine, monoisopropanolamine, diethylethanolamine, ethyl diethanolamine, secondary alkanolamines: diethanolamine, diisopropanolamine, 2-(methylamineo) ehtano, morpholine, ternary alkanolamines: triethanolamine, tri-isopropylamine), alkylamines (e.g. primary alkylamines, monomethylamine, monoethylamine, monopropylamine, monobutylamine, monopentylamine, cyclohexylamine, secondary alkylamines: dimethylamine), alkyleneamines (e.g. primary alkylene amines: ethylenediamine, propylenediamine, triethylenetetramine), and mixtures thereof. Preferred examples of such materials include monoethanolamine, ethylenediamine, triethylenetetramine and mixtures thereof. The most preferred is monoethanolamine. The amount of the organic amine preferably ranges from 0.01% to 20%, and most preferably from 0.2% to 2%.

The source solution may also contain a biocide such as 2-Methyl-4-isothiazolin-3-one (MIT) or 2-Methyl-4-Isothiazolin-3-one Hydrochloric acid (C4H4NOS, HCl), (MIHCA). The concentration of the biocide is preferably from 1 ppm to 100 ppm, and more preferably form 30-70 ppm. Other biocides may be used as well. Biocides do not affect the particle removal efficiency, but prevent any bacterial growth in the cleaning solution.

Surfactants can also be added. Typically non-ionic surfactants are preferred. Preferred surfactants are the ethylene oxide type surfactants with a general structure $C_nH_{2n+1}O(C_2H_4O)_mH$. A good non-ionic surfactant is $C_{12}H_{25}O(C_2H_4O)_{11}H$. The concentration of the surfactant in the concentrated source solution will be preferably between 0.1% and 5%. Most preferably concentrations are around 0.5% for the concentrated source solution. The concentration after dilution with water and when used for cleaning the surfaces will be preferably between 0.0001 to 0.5% by weight. This is between 1 ppm and 5000 ppm by weight. More preferably the concentration after dilution will be between 10 ppm and 500 ppm. The surfactants do not substantially improve the particle removal efficiency, but may be added to improve the wetting capability of the solution. This is especially useful on hydrophobic surfaces.

Sequestering agents or complexing agents can also be added. Preferred sequestering or complexing or chelating agents are the nitrogen-containing carboxylic acids such as ethylenediaminetetraacetic acid (EDTA) and diethylenetriaminepentaacetic acid (DTPA). The concentration of the sequestering agent after dilution with water and when used for cleaning the surfaces will be preferably between 10 ppm and 500 ppm. Sequestering agents do not substantially improve the particle removal efficiency, but can be added to improve the metallic impurity deposition of the cleaning operation.

The solutions of this invention with polycarboxylate polymers remove particles substantially better than conventional ammonium hydroxide only solutions, known in the prior art for cleaning imprint molds.

The solution with polycarboxylate polymers or ethoxylated polyamines with or without amines, surfactants and or sequestering agents and other chemicals added can be contacted on the substrate of the hard disk or imprint mold or read/write head assembly part in a bath or immersion type apparatus, which can be single substrate or batch, or in a spinning substrate type apparatus, which can also be single substrate or batch or in a horizontal conveyor belt style apparatus or in any other apparatus type suitable for contacting one or more substrates or parts with a solution with polycarboxylate polymers or ethoxylated polyamines with or without $NH_4OH$ or KOH or other chemicals added and with or without amines, surfactants and or sequestering agents added.

Finally, it is clear that other substances may be added to the solution with polycarboxylate polymers with or without $NH_4OH$ or KOH or any other base. Adding other substances to this solution does not constitute a deviation from the idea of the current invention. Specifically $H_2O_2$ may be added to the solution.

The removal efficiency of more tenaciously adhered particles on the surface can be improved from the simple contacting with a polycarboxylate polymer or ethoxylated polyamine containing solution of this invention in several ways.

Such known additional ways include, for example, megasonics, an aerosol spray and a scrubbing action with a PVA brush. Indeed, the megasonics act by causing cavitation events due to the dissolved gases in the solution. These cavitation events cause a mechanical agitation on the adhered particles and hence dislodge them from the surface of the disk or the imprint mold or the read/write head assembly part. The megasonics also act by reducing the boundary layer. An aerosol spray technique exerts a mechanical force onto adhered particles by causing a very fast flow of liquid over the surface of the disk or imprint mold or read/write head assembly part. An aerosol spray technique can be set up such that it only exerts a force on large particles and large features. Hence, an aerosol spray technique can be selective for exerting a force on large particles and large features, but not on small particles and small features, which are very fragile. An aerosol spray technique also reduces the boundary layer in a similar way like the megasonics.

In addition, after the cleaning is finished, it is advantageous to follow up the cleaning sequence with an improved DI water rinse. The improved DI water rinse can consist of a megasonics without gas to avoid cavitation or a megasonics at high frequency. The improved DI water rinse can also be a rinse with a spray. A spray rinse can be a regular water spray or an aerosol spray. A regular water spray is effective at high flows.

The temperature of the cleaning solution during cleaning of hard disks or imprint molds or read/write head assembly parts can be any temperature from 0 degrees C. to 100 degrees c with room temperature preferred because of its ease and economical advantage. For absolute best particle performance lower temperatures are even preferred. Preferred temperatures for best particle performance are between 1 degrees C. and 20 degrees C. and more preferred from 3 degrees C. to 15 degrees C. and most preferred from 5 degrees C. to 12 degrees C. Lower temperatures are also advantageous to reduce the surface etching amount. At lower temperatures a higher pH can be used with equivalent etching amount as one would have at a higher temperature, but at a considerable lower pH. The higher pH is improving the cleaning performance.

The subsequent rinsing can also be carried out at subambient temperatures to improve the particle performance.

After cleaning with the solution of the current invention containing either a polycarboxylate polymer or an ethoxylated polyamine, it is desirable to remove all of the polycarboxylate polymers, or all of the ethoxylated polyamines. Normally this can be done adequately by thorough rinsing. If absolutely the lowest levels of remains are necessary, especially after using the polycarboxylate polymer solutions, then a two stage cleaning can be used. The first stage is a $NH_4OH$ based clean; and the second stage is an HCl based cleaning (or HCl rinse water can simply be used). Alternatively the $NH_4OH$ based step can be skipped and the rinsing can be acidified with HCl. This is particularly useful for the ethoxylated polyamine solutions. Alternatively to $NH_4OH$, any other base can be used as well.

For purposes of illustration, the principles and methods of the present invention for a concentrated solution and a cleaning solution and a method and apparatus for cleaning the front side of the disk and/or the back side of the disk and/or the bevel of the disk will now be described. It can also be used for cleaning imprint molds or read/write head assembly parts.

A typical make-up of a concentrated source solution according to the invention for use in a 5:1 solution and when the copolymer is supplied together with the $NH_4OH$ as one blended source solution is shown in Example 1:

|  | Percent (%) |
|---|---|
| 50/50 acrylic/maleic copolymer in the acid form with an average molecular weight of 3000 Daltons | 3.5%-w |
| $NH_4OH$ (26%-w as $NH_3$) | Balance |

This concentrated solution can be made off-site and be transported to the fab. In the fab, it is typically diluted with water with a factor 5:1 $H_2O$:concentrated solution of Example 1 to a final cleaning concentration of 3.7% $NH_4OH$ (as $NH_3$), 0.5% acrylic/maleic copolymer. $H_2O_2$ can be added in such cleaning solutions in the same or higher amount as $NH_4OH$. It has to be remarked that the pH of these final solutions will be slightly less than what would be obtained without the 50/50 acrylic/maleic copolymer (in the acid form) since the 50/50 acrylic/maleic copolymer contains acidic carboxylic groups. One can compensate for that by using the appropriate slightly higher amount of the source solution to end up with the same final pH as one would have when using a 5:1 solution made up of $H_2O$:$NH_4OH$. In the case of a 5:1 solution, this difference is however negligible. This compensation is not necessary if the 50/50 acrylic/maleic copomyler would be supplied in a neutral form. The final $NH_4OH$ concentration at 26%-w will be slightly lower than the 28%-w as is more common, when the copolymer will be added already dissolved in water to 28%-w standard solution. When the copolymer will be added in solid form, the 28-w % concentration can be maintained closer.

A typical make-up of a concentrated solution according to the invention for use in a 20:1 solution is shown in Example 2:

|  | Percent (%) |
|---|---|
| 50/50 acrylic/maleic copolymer in the acid form with an average molecular weight of 3000 Daltons | 12%-w |
| $NH_4OH$ (21%-w as $NH_3$) | Balance |

This concentrated solution of Example 2 can be made off-site and be transported to the fab. In the fab, it is typically diluted with water with a factor 1:20 to a final cleaning concentration of 1% $NH_4OH$ (as $NH_3$) and 0.6% acrylic/maleic copolymer. $H_2O_2$ can also be added. $H_2O_2$ would typically be added in the same or higher amount as $NH_4OH$ to make a 20:1:1 solution $H_2O$:$H_2O_2$:source solution of Example 2. In this case, due to the acidifying effect of the acrylic/maleic copolymer (when supplied in the acid form), the pH of a 20:1:1 $H_2O$:$H_2O_2$:source solution of example 2 is in a similar range as the pH of a 20:1:0.3 solution of $H_2O$:$H_2O_2$:$NH_4OH$ (28% $NH_3$). One can compensate for that if desired by decreasing the $H_2O_2$ concentration or by increasing the concentration of the source solution of example 2.

A typical make-up of a concentrated solution according to the invention for use in a 30:1 solution is shown in Example 3:

|  | Percent (%) |
|---|---|
| 50/50 acrylic/maleic copolymer in the acid form with an average molecular weight of 3000 Daltons | 15.6%-w |
| NH4OH (19%-w as $NH_3$) | balance |

This concentrated solution of Example 3 can be made off-site and be transported to the fab. In the fab, it is typically diluted with water with a factor 1:30 to a final cleaning concentration of 0.64% $NH_4OH$ (as $NH_3$) and 0.5% acrylic/maleic copolymer. $H_2O_2$ can also be added. In order to get the same pH as one would get for a 30:1:1 $H_2O$:$NH_4OH$(28%):$H_2O_2$(30%) solution, $H_2O_2$ would typically be added in the same or higher amount as the free $NH_4OH$ which is not used to neutralize the copolymer, when the copolymer is added in the acid form. That would be the case for a mixing ratio of about 30:1:0.22 or alternatively said a mixing ratio of 136:4.5:1 for $H_2O$:concentrated solution of example 3: $H_2O_2$ (30%). The concentration of the $H_2O_2$ may also be doubled e.g. to roughly a 70:2:1 $H_2O$:concentrated solution of example 3:$H_2O_2$ solution. This will have a pH comparable to a conventional 30:1:2 $H_2O$:$NH_4OH$:$H_2O_2$ solution.

A typical make-up of a concentrated solution according to the invention is shown in Example 4:

|  | Percent by volume (%) |
|---|---|
| 50/50 acrylic/maleic copolymer in the acid form with an average molecular weight of 3000 Daltons | 15% |
| TMAH | 5% |
| Water | Balance |

This concentrated solution can be made off-site and be transported to the fab. This solution can be diluted in the fab with water and/or other chemicals.

Typically, pH ranges between 8 and 14 and preferably between 9 and 12 and most preferably between 10 and 11 are very good for cleaning particles in combination with the acrylic/maleic copolymer or the acrylic homopolymer. Other substances can be used instead of $NH_4OH$ to get a similar pH. Typical other substances used to increase the pH are e.g. TMAH (as in example 4) and choline. When alkaline metals are of no concern, KOH or NaOH can be used. Other substances to get to the appropriate pH range such as but not limited to $K_2CO_3$ and $Na_2CO_3$ can be sued as well in such cases.

An example of a single imprint mold spin-spray cleaning chamber will now be given in more detail specifically for cleaning imprint molds. Referring to FIG. 1, the spin chamber 20 contains the imprint mold 21, being held horizontally by an imprint mold holder 22, connected to a motor 23. The imprint mold is held with the front side of the imprint mold facing down. The motor and imprint mold holder assembly is mounted in a bowl 24 containing a liquid diverter 25, an exhaust 26 and a drain 27. A nozzle 28 is mounted to direct the liquid solution with the acrylic/maleic copolymer or acrylic homopolymer preferably at ambient or subambient temperature onto the spinning imprint mold 21. The nozzle 28 is directed to dispense the liquid from below the imprint mold while the imprint mold is facing front-side down. In this way, gravity helps in transporting the particles away from the surface, out of the boundary layer and into the flowing stream. The nozzle 28 is fed from a mixer 29 where a solution of acrylic/maleic copolymer or acrylic homopolymer and NH$_4$OH and DI water is mixed in the desired ratio. The solution is fed from line 30. The chiller 32 may cool the incoming DI water from line 33 down to a desired subambient temperature. In addition to the nozzle 28, which can supply subambient temperature liquid onto the spinning substrate, another nozzle (not shown) can be used to supply an accelerated atomized aerosol of the solution onto the imprint mold. This accelerated nozzle helps in bringing the solution in close proximity to the adhered particles on the imprint mold.

A close up of such an accelerated atomized aerosol nozzle configuration is shown in FIG. 2. Referring to FIG. 2, a nozzle 100 is shown with nozzle body 103 and liquid inlet 101 for the solution with acrylic/maleic copolymer or acrylic homopolymer. Inlet 102 is the gas inlet. A variety of accelerating gases can be used, but most conveniently $N_2$ or CDA (Compressed Dry Air) can be used. The liquid inlet 101 is connected to the liquid outlet 106. The gas inlet 102 is connected to gas outlets 104 and 105, which can be a single circular outlet. The gas coming out of outlets 104 and 105 atomizes and accelerates the atomized droplets 108 of the liquid coming out of outlet 106. The atomized aerosol containing acrylic/maleic copolymer or acrylic homopolymer is jetted towards the substrate surface.

Even though the chiller 32 in spin chamber 20 is positioned before the mixer 29, the mixing of acrylic/maleic copolymer or acrylic homopolymer and DI water can be done before the chiller. Even though in FIG. 1, the atomized aerosol is supplied with a solution of acrylic/maleic copolymer or acrylic homopolymer, the aerosol can also be supplied with simple DI water. In this case the aerosol is merely used to create a motion in the solution already on the imprint mold or the aerosol jet is used to remove large particles selectively as is known in the prior art.

After the imprint mold contacting with a solution of acrylic/maleic copolymer or acrylic homopolymer, the imprint mold can preferably be rinsed with subambient temperature DI water. Indeed, the rinsing of the imprint mold with subambient temperature DI water will reduce the final particle count. The drying can be done with any of the known methods for drying imprint molds. In batch mode the most preferred drying method is the surface tension gradient method, preferably using a vapor of IPA. However, a spin dry method can also be used. In a single imprint mold mode a surface tension gradient drying method can be used or a simple spin dry method can be used. Any other method to dry a substrate without adding substantial contamination during the process of drying, i.e. any known clean drying method, can also be used. If a surface tension gradient drying method is used, a vapor of IPA will be blown in the center of the imprint mold, while the imprint mold is facing front-side down. This IPA nozzle is not shown in FIG. 1.

Even though the simple act of contacting the surface of a substrate with a solution of acrylic/maleic copolymer or acrylic homopolymer can remove submicron particles very effectively, the removal efficiency can be improved with an accelerated jet, and it can also be done by the use of megasonics. One such apparatus, a single imprint mold spin-spray tool, is shown in FIG. 3. In the single imprint mold spin-spray apparatus 40 of FIG. 3, an imprint mold holder 42 connected to a motor 43 holds a imprint mold 41. The imprint mold can be held with the front side of the imprint mold facing down. Positioned below the imprint mold is a sonic transducer 48. The sonic transducer is e.g. made of stainless steel or aluminum and is preferably coated with PFA. On the backside of the sonic transducer, PZT crystals 49 are bonded to generate the sonic waves. The PZT crystals are connected to a megasonic frequency power supply (not shown) and protected in a housing to isolate the PZT crystals from the cleaning liquids (not shown). Closer to the center of the imprint mold, there is a liquid feed through 51, which is connected to a chemical feed line 50. This chemical feed line supplies chemicals or DI water through the sonic transducer 48 to the backside of the imprint mold 41. The PZT crystals 49 generate the sonic waves in a frequency range of 200-6000 kHz. Conventionally frequency ranges between 700 kHz and 1.8 MHz are being used. This is commonly used for megasonics cleaning. However, any frequency range of 200-6000 kHz can be used.

The imprint mold 41 with imprint mold holder 42, motor 43 and sonic transducer 48 is mounted inside a bowl 44 with liquid diverter 45, drain 47 and exhaust 46. The sonic transducer 48 can have various shapes as is shown in FIG. 4. In FIG. 4, a linear transducer 60, a full imprint mold disk shaped transducer 70 and a pie-shaped transducer 80 are shown. In each transducer 60, 70 and 80, the outline of the imprint mold 41 is shown and the chemical feed through 51 is shown.

The final rinse method is very important, since the final rinse needs to remove all of the acrylic/maleic copolymer or acrylic homopolymer from the surface. The final rinse method can be preferably carried out with megasonics with or without gas to avoid damage, high frequency to avoid damage. The final rinse can also be carried out with an atomized spray. The final rinse is preferably carried out with subambient temperature water.

In addition, the final rinse with subambient temperature water can be combined with a surface tension gradient particle removal and drying technique. Using an IPA vapor of some sort usually generates the surface tension gradient. The subambient temperature water can be contacted to the front side of the imprint mold first, followed by a surface tension gradient cleaning and or drying.

In view of this disclosure, a representative embodiment of the present invention is a method for cleaning submicron particles off a surface of a substrate. The method comprises the step of contacting a surface of the substrate with a cleaning solution comprised of a polycarboxylate polymer, such as one of the polycarboxylate homopolymers or copolymers described previously with respect to Formulas 1-6 (or an ethoxylated polyamine, or an ethoxylated quaternized diamine described previously with respect to Formulas 7-9). Generally, the substrate is an electronic substrate meaning that it is a semiconductor wafer or a storage medium, such as a hard disk, or a substrate used in manufacturing wafers or storage media, such as a photomask or an imprint mold, or read/write head assembly parts. The method may be used to clean a single substrate or more than one substrate at a time. An optional step in the method is to apply acoustic energy to the cleaning solution while the cleaning solution is in contact with the surface. Another additional optional step in the method is to remove the cleaning solution from the surface by rinsing the surface with a rinsing solution, such as an aqueous solution, with or without the application of acoustic energy to the rinsing solution while the surface is being rinsed. In this context acoustic energy means acoustic energy of any appropriate frequency, such as ultrasonic energy or megasonic energy.

Generally, the surface of the substrate has a plurality of particles adhered to it and at least some of the particles are carried away from the surface when the cleaning solution is removed from the surface, such as by rinsing. In a particularly useful application, the particles are submicron particles, meaning that the particles are smaller than one micrometer. In another particularly useful application, the surface of the substrate has at least one electronic feature having a dimension of less than 0.3 micrometers formed on it. Examples of such electronic features are the fine patterns on semiconductor wafers, such as the transistor gates or interconnect lines formed on the surface of a semiconductor wafer. Other examples include the patterns formed in imprint molds, which are the reverse image of the features on a substrate, such as a semiconductor wafer, or the features formed on a photomask that are reduced in the photolithographic process.

Regardless of whether or not the surface of the substrate contains an electronic feature, the cleaning method of the present invention is an isotropic cleaning method that does not utilize a pad to abrasively remove material from the surface of the substrate as is done in a planarization process, such as CMP.

Another embodiment of the present invention is a cleaning solution for cleaning substrates, including electronic substrates, and that can be used in the method described above. The cleaning solution comprises a polycarboxylate polymer (or an ethoxylated polyamine, or an ethoxylated quaternized diamine).

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true scope of the invention.

What is claimed is:

1. A method for removing submicron particles from a surface of a hard disk substrate, comprising contacting the surface with a cleaning solution comprised of a polycarboxylate polymer and a base chosen from the group consisting of ammonium hydroxide and a quaternary ammonium compound, the solution having a pH of 8 or higher and not including hydrogen peroxide.

2. The method of claim 1 wherein the polycarboxylate polymer comprises either homopolymers or copolymers of acrylic acid, methacrylic acid, maleic acid, fumaric acid, or itaconic acid.

3. The method of claim 1 wherein the polycarboxylate polymer comprises a polymer that is prepared from either monomers having the general formula:

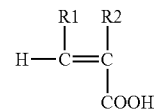

where R1 and R2 is chosen from a hydrogen atom or a methyl radical, or from monomers having the following formula:

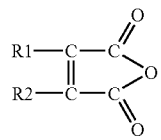

where R1 and R2 are independently H, an alkyl or a phenyl group.

4. The method of claim 1 wherein the polycarboxylate polymer consists essentially of an acrylic acid homopolymer.

5. The method of claim 1 wherein the polycarboxylate polymer has an average molecular weight between 300 and 1,000,000 Daltons.

6. The method of claim 1 wherein the polycarboxylate polymer is used in a concentration between 0.001%-6% by weight.

7. The method of claim 1 wherein the solution has a pH in the range of 9-12.

8. The method of claim 1 further comprising:
    after the surface has been contacted with the cleaning solution, removing the cleaning solution from the surface.

* * * * *